(12) United States Patent
Aviram (10) Patent No.: US 7,824,619 B1
(45) Date of Patent: Nov. 2, 2010

(54) MOLECULAR SENSORS FOR EXPLOSIVES

(76) Inventor: Ari Aviram, 444 Bramblebush Rd., Croton on Hudson, NY (US) 10520

( * ) Notice: Subject to any disclaimer, the term of this patent is extended or adjusted under 35 U.S.C. 154(b) by 1487 days.

(21) Appl. No.: 11/146,810

(22) Filed: Jun. 7, 2005

Related U.S. Application Data (60) Provisional application No. 60/577,617, filed on Jun. 7, 2004.

(51) Int. Cl.
*G01N 30/96* (2006.01)
*G01N 27/16* (2006.01)
*G01N 27/00* (2006.01)
*H01L 21/8238* (2006.01)
*H01L 21/20* (2006.01)
*H01L 21/00* (2006.01)

(52) U.S. Cl. .............. 422/88; 422/96; 422/98; 438/233; 438/141; 438/151

(58) Field of Classification Search .......... 422/88, 422/96, 98; 438/233, 141, 151
See application file for complete search history.

(56) References Cited

U.S. PATENT DOCUMENTS

| | | | | |
|---|---|---|---|---|
| 4,312,936 | A * | 1/1982 | Engler et al. | 430/296 |
| 5,645,710 | A * | 7/1997 | Shieh | 205/778 |
| 6,316,268 | B1 * | 11/2001 | Yang et al. | 436/106 |
| 6,670,286 | B1 * | 12/2003 | Yang et al. | 438/780 |
| 6,872,786 | B2 | 3/2005 | Murray et al. | 525/326.7 |
| 2006/0183165 | A1 * | 8/2006 | Zhang et al. | 435/7.9 |
| 2009/0090905 | A1 * | 4/2009 | Tokita et al. | 257/40 |

OTHER PUBLICATIONS

Svenstrup, N., et al., "The Chemistry of TTFTT; 1: New Efficient Synthesis and Reactions of Tetrathiafulvalen- 2.3,6,7-tetrathiolate (TTFTT): An Important Building Block in TTF-Syntheses," *Synthesis*, 809-812 (Aug. 1994).

Park, H., et al., "Fabrication of metallic electrodes with nanometer separation by electromigration," *Applied Physics Letters*, 75(2): 301-303 (Jul. 12, 1999).

(Continued)

*Primary Examiner*—Lore Jarrett
(74) *Attorney, Agent, or Firm*—Arendt &Assoc. IP Group; Jacqueline M. Arendt; Richard W. Wagner (57) ABSTRACT

The present invention relates to a molecular sensor for detecting the presence of a target analyte comprising a nitro-containing explosive molecule, the sensor comprising: a support substrate; a pair of electrodes comprising (i) a first electrode and (ii) a second electrode, wherein at least one of (i) and (ii) is at the substrate; an electron donor (ED) molecule capable of forming an electron donor-acceptor (EDA) complex with the nitro-containing explosive molecule; and wherein the ED molecule is disposed between the electrodes and is attached to each electrode by an alligator clip comprising a pendant group, thereby forming a nanojunction between the electrodes; a detection means operably connected to the pair of electrodes, the detection means capable of detecting a change in the electrical resistance or in the capacitance of the sensor when the ED molecule forms an EDA complex with the explosive molecule, the sensor thereby detecting the presence of the explosive molecule. Also disclosed are methods of making and methods of using the sensor.

33 Claims, 1 Drawing Sheet

OTHER PUBLICATIONS

Guillorn, M., et al., "Fabrication of dissimilar metal electrodes with nanometer interelectrode distance for molecular electronic device characterization," *J. Vac. Sci. Technol. B* 18(3): 1177-1181 (May/Jun. 2000).

Nuzzo, R.G. and Allara, D. L., "Adsorption of Bifunctional Organic Disulfides on Gold Surfaces," *J. Am. Chem. Soc.*, 105: 4481-4483 (1983).

Inokuchi, H., et al., "New Organic Superconductors," *Angew. Chem.*, 100: 1817-1821 (1988).

Gomar-Nadal, E., et al., "Self-Assembled Monolayers of Tetrathiafulvalene Derivatives on Au(111): Organization and Electrical Properties," *J. Phys. Chem. B*: 108: 7213-7218 (2004).

Reed, M.A., et al., "Conductance of a Molecular Junction," *Science*, 278: 252-253 (Oct. 1997).

Allara, D. L., et al., "Evolution of Strategies for Self-Assembly and Hookup of Molecule-Based Devices," *Annals New York Academy of Sciences*, 852: 349-370 (1983).

Saito, G., et al., "Two-Dimensionality and Suppression of Metal-Semiconductor Transition in a New Organic Metal with Alkylthio Substituted TTF and Perchlorate," *Solid State Communications*, 42,(8): 557-560 (1982).

Cui, X.D., et al., "Reproducible Measurement of Single-Molecule Conductivity," *Science*, 294: 571-575 (2001).

Simonsen, K., et al., "Sequential Functionalisation of Bis-Protected Tetrathiafulvalene-dithiolates," *Synthesis*, 407-418 (1996).

* cited by examiner

MOLECULAR SENSORS FOR EXPLOSIVES

RELATED APPLICATION

This application claims the benefit of U.S. Provisional Application No. 60/577,617 filed on Jun. 7, 2004, the teachings of which are incorporated herein by reference in their entirety.

BACKGROUND OF THE INVENTION

A number of methods for detecting explosives are currently available. At present, the most commonly employed method utilizes the sense of smell of an animal such as a dog, pig, or a pouched rat trained for this purpose. The noses of these animals can detect minute amounts of airborne-explosives molecules that leak from sealed containers, such as mines or bombs.

Another approach to explosives detection is based on mass-spectroscopy of air samples. Although feasible for use outside a laboratory, currently available mass spectrometric systems tend to be an inconvenient size for use in the field.

Another technique relies upon nuclear quadrupole resonance (NQR) signals.

Thus the need exists for a fast, reliable, improved sensor for detecting minute concentrations of air-borne explosive molecules.

SUMMARY OF THE INVENTION

The invention inter alia includes the following, alone or in combination. The present invention relates to compositions and devices useful for detection of small amounts of airborne molecules of explosives, and methods of using the devices to detect an explosive. In addition, the invention relates to methods for the fabrication of electrode nanojunctions for use in the detection of target analytes comprising a nitro-containing explosive molecule.

It has now been discovered that electron-donor molecules such as, for example, tetrathiafulvalene, tetraselenafulvalene, dithiophene-tetrathiafulvalene, tetrathiatetracene, N,N,N', N'-tetramethyl-phenylenediamine, trimethoxybenzene, and tetraminoanthraquinone form donor-acceptor complexes with target analytes containing nitro-containing explosives such as TNT, and that molecules possessing this property can be used to form molecular-electronic sensors for airborne molecules of explosives that contain nitro groups.

The molecular-electronic sensors are fabricated from pairs of electrodes connected to one or several donor molecules by specific organic groups that form chemical bonds between the molecule and the metal or semiconducting electrodes.

One aspect of the present invention is directed to nanometer-size structures that can bind single molecules of explosives with a detectable change in the conductivity and the capacitance of the device. One embodiment of the invention is a device comprising a metal-molecule-metal structure, that can be addressed by macroscopic electrical contacts.

According to an embodiment of the invention, a sensor for detecting the presence of a target analyte comprises a nitro-containing explosive molecule, the sensor comprising: a support substrate; a pair of electrodes comprising (i) a first electrode and (ii) a second electrode, wherein (i) and (ii) comprise the same or different materials, and wherein at least one of (i) and (ii) is at the substrate; an electron donor molecule capable of forming an electron donor-acceptor complex with the nitro-containing explosive molecule; and wherein the electron donor molecule is disposed between the first electrode and the second electrode and is bonded to the first electrode and to the second electrode, thereby forming a nanojunction between the first and second electrodes; a detection means operably connected to the pair of electrodes, the detection means capable of detecting a change in the electrical resistance or in the capacitance of the sensor when the electron donor molecule forms an electron donor-acceptor complex with the nitro-containing explosive molecule, the sensor thereby detecting the presence of the nitro-containing explosive molecule.

In one embodiment of the disclosed sensor, the electron donor molecule comprises a first pendant functional group that is bonded to the first electrode and a second pendant functional group that is bonded to the second electrode, and the first and second pendant functional groups can be the same or different.

The invention inter alia also includes a method for detecting the presence of a target analyte comprising a nitro-containing explosive molecule, the method comprising:

a) providing a sensor comprising: a support substrate; a pair of electrodes comprising (i) a first electrode and (ii) a second electrode, wherein (i) and (ii) comprise the same or different materials, and wherein at least one of (i) and (ii) is at the substrate; an electron donor molecule capable of forming an electron donor-acceptor complex with the nitro-containing explosive molecule; and wherein the electron donor molecule is disposed between the first electrode and the second electrode and is bonded to the first electrode and to the second electrode, thereby forming a nanojunction between the first and second electrodes; a detection means operably connected to the pair of electrodes, the detection means capable of detecting a change in the electrical resistance or in the capacitance of the sensor when the electron donor molecule forms an electron donor-acceptor complex with the nitro-containing explosive molecule;

b) exposing the electron donor molecule of the sensor to an environment containing the nitro-containing explosive molecule such that the nitro-containing explosive molecule contacts the electron donor molecule;

c) allowing the electron donor molecule to form an electron donor-acceptor complex with the nitro-containing explosive molecule, the formation of the electron donor-acceptor complex resulting in the sensor undergoing a detectable change in electrical resistance or in capacitance; and d) detecting any change in the electrical resistance or in the capacitance of the sensor, the detected change being indicative of the presence of the nitro-containing explosive molecule in the environment.

In another aspect, the invention relates to a method of making a sensor for detecting the presence of a target analyte comprising a nitro-containing explosive molecule, the method comprising:

a. providing a support substrate;

b. forming, on a surface of the substrate, a pair of electrodes comprising a first electrode and a second electrode and having an inter-electrode distance of from about 0.5 nanometer to about 10 nanometers;

c. disposing, between the first electrode and the second electrode, an electron donor molecule capable of forming an electron donor-acceptor complex with the nitro-containing explosive molecule, the electron donor molecule comprising a first pendant functional group capable of bonding to the first electrode and a second pendant functional group capable of bonding to the second electrode, and wherein the first and second pendant functional groups are the same or different;

d. allowing the first and second pendant functional groups to bond to the first and second electrodes, respectively, thereby bridging the inter-electrode distance and forming a nanojunction between the first and second electrodes;

e. operably connecting to the pair of electrodes a detection means capable of detecting a change in the electrical resistance or in the capacitance of the sensor when the electron donor molecule forms an electron donor-acceptor complex with the nitro-containing explosive molecule.

Yet another embodiment of the invention is a method of making a sensor for detecting the presence of a target analyte comprising a nitro-containing explosive molecule, wherein the method comprises:

a) providing a support substrate;

b) depositing a first electrode on a surface of the substrate;

c) depositing, on the first electrode, an electron donor molecule capable of forming an electron donor-acceptor complex with the nitro-containing explosive molecule, the electron donor molecule oriented such that the length of the molecule is approximately perpendicular to the substrate surface;

d) depositing a second electrode on the electron donor molecule, the second electrode positioned such that the second electrode is not in contact with the substrate and is not parallel to the first electrode, thereby forming a nanojunction comprising two electrodes and an electron donor molecule bridging a gap between the two electrodes; and e) operably connecting to the pair of electrodes a detection means capable of detecting a change in the electrical resistance or in the capacitance of the sensor when the electron donor molecule forms an electron donor-acceptor complex with the nitro-containing explosive molecule.

The present invention has many advantages. A sensor according to various embodiments of the invention is very sensitive towards nitro-containing explosive molecules and is able to detect miniscule amounts of explosives. For example, only one TNT molecule is needed to activate the sensor. A disclosed sensor can be small enough to be located on a chip; to be hand-held or carried; or to be attached, for example, as a badge to a human or other animal. A disclosed sensor comprises a nanometer-size structure that can bind single molecules of explosives with a detectable change in the conductivity and the capacitance of the sensor. A disclosed sensor is capable of mimicking the specificity and sensitivity of an animal's olfactory system for detection of minute amounts of airborne vapors of explosives, for example, that leak from sealed containers, such as mines or bombs. A disclosed sensor is easy to operate and is normally dormant; but in the presence of explosives, its electrical conductivity and capacitance change markedly, whereupon the change can be detected and transmitted as an electronic signal. The present invention thus provides a sensor that can quickly communicate the presence of minute amounts of explosive molecules to remote locations, for example through a computer network.

BRIEF DESCRIPTION OF THE DRAWINGS

The foregoing and other objects, features and advantages of the invention will be apparent from the following more particular description of illustrative embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows. It will be understood that the particular embodiments of the invention are shown by way of illustration and not as limitations of the invention. At the outset, the invention is described in its broadest overall aspects, with a more detailed description following. The features and other details of the compositions and methods of the invention will be further pointed out in the claims.

The present invention relates to a sensor with components as generally described above, the sensor useful for detecting the presence of a target analyte comprising a nitro-containing explosive molecule, and to methods of making and methods of using the sensor to detect the presence of such airborne explosive molecules.

Also disclosed are examples of materials required to form functioning explosives-sensing devices. The electron-donor (ED) molecules described herein comprise the heart of the sensor device because the ED molecules capture the nitro-explosives-molecules and form specific complexes with them. The complexation is also accompanied by detectable changes in the conductivity and dielectric-constant of the molecules. The described device has a relatively high electrical resistance of about 1.25 giga ohms, which drops precipitously when the ED molecules form complexes with the explosives molecules. The change in conductivity is accompanied by a change in the capacitance of the device. Both changes are measurable, and can be used for detection of the analyte.

The sensor can be fabricated from one or several metal-molecule-metal nanojunctions in parallel or in series. A detection means capable of detecting a change in the electrical resistance or in the capacitance of the sensor when the ED molecule forms an EDA complex with the nitro-containing explosive molecule is operably connected through macroscopic electrical contacts to the pair of electrodes attached to the ED molecule. In response to the change in capacitance of the sensor, in one embodiment of the invention, the detection means transmits a signal to a processing unit or signal analyzer. The analyzer can be coupled to a wireless communication interface, for example, a radio frequency (RF) interface.

Electron-Donor-Acceptor Complexes

As the name implies, electron donor-acceptor (EDA) complexes comprise a donor and an acceptor molecule. The donor donates one electron or a pair of electrons (unshared or shared) to the acceptor, which can be a metal atom or a molecule. In a case wherein the acceptor is an organic molecule, the exact bonding characteristics are not known. However, the existence of EDA compounds is well documented. One characteristic property of EDA complexes is their electronic spectrum. In all cases, new absorption bands appear, that are not present in either the donor or the acceptor. A very famous EDA complex acceptor is picric acid, also known as trinitrophenol (TNP), of formula:

a highly explosive compound, especially when dry. Picric acid forms addition compounds with many aromatic hydrocarbons, aromatic amines, olefines and other compounds. These addition-compounds are usually solids with definite melting points and are used as derivatives of compounds for identification purposes.

The structural property of TNP that makes this compound such a strong electron acceptor are the three nitro groups on the aromatic ring. Dinitrophenol (DNP) and Trinitrotoluene (TNT) are also members of this electron acceptor group, and form EDA complexes as described above. Other polynitro compounds such as trinitrobenzene (TNB), and cyclonite (hexahydro 1,3-trinitro-1,3,5-triazine, RDX have similar properties and are among the most important acceptors for EDA complexes (1). The afore-mentioned nitro-containing electron acceptor molecules, including TNP, DNP, TNT, TNB, and RDX, are non-limiting examples of target analytes containing explosive molecules that can be detected by a disclosed sensor.

Nanofabrication

Production of molecular circuits requires the fabrication of electrode nanojunctions with inter-electrode distances of a few nanometers. The size of the nanojunction is determined by the size of the molecule that must be embedded in the junction gap. The precise matching of the molecular length with the electrode gap is crucial to the success of the fabrication.

Thus, there are two opposing demands: The inter-electrode distances, also referred to as "gaps", are limited by the constraints of lithography technology, while the sizes of the molecules are limited by the resources and time allowed to the chemistry team. In one embodiment, the nanojunction can bridge an inter-electrode distance or gap of from about 0.4 nanometer to about 20 nm, or a gap of from about 0.5 nanometer to about 5 nanometer.

E-beam lithography is a sequential method for pattern formation; despite being extremely slow, it is very well suited for sensor fabrication. This technology can produce metal-gap-metal structures with a 4-nm gap (2).

Another technique for forming nanojunctions is the break-junction technique (3). Metal is first deposited in the form of a wire, the wire having a diameter of from about 4 nanometers (nm) to about 10 nm, on a flexible insulating substrate. When the substrate is bent, the metal wire breaks, and a gap forms. The dimension of the gap can be controlled by the curvature of the bend (from 1-nm to 4-nm) (3).

Yet another technique for forming metal-gap-metal structures relies on electrical migration of gold. For example, when a gold wire (about 10-nm wide) is subjected to electrical current, it breaks. The gaps formed by this method are about 1-nm long (4).

In one embodiment of the disclosed sensor, at least two electron donor molecules are disposed between the first electrode and the second electrode and the molecules are in parallel.

Connecting Molecules to Electrodes

As the term is used herein, an "electrode" is a conductive or semi-conductive composition that is an electron transfer moiety. Preferred electrodes are known in the art and include, but are not limited to, the electrodes described herein.

In one embodiment of the invention, at least one of the first electrode and the second electrode is in the form of a wire.

Examples of preferred electrodes for use in the disclosed sensor include: a substance chosen from at least one of gold, platinum, palladium, aluminum, silicon, carbon, Se—Au, and Te—Au; carbon chosen from at least one of glassy carbon, graphite, carbon paste, and carbon nanotube; gold in the form of gold nanoparticles; and a conducting oxide. As the term is used herein, "gold nanoparticle" refers to a cluster of gold atoms. Examples of suitable conducting oxides include platinum oxide, titanium oxide, tin oxide, indium tin oxide, and palladium oxide.

Other examples of preferred electrodes can be a semiconductor chosen from at least one of silicon doped with at least one element listed in the Periodic Table in Group II, Group III, and Group V; and a heterocompound chosen from at least one of a heterocompound comprising elements from Group II, Group III, Group IV, and Group V. Other examples of suitable electrodes include gallium arsenide, and a conducting polymer filament.

Self-assembly is a technique that is used extensively in surface science for attaching molecules to surfaces. Certain chemical groups have an affinity for some specific metals and bind spontaneously to them: for example, the specific attachment of thiol (SH) groups to gold (5) and the attachment of COOH groups to aluminum. Thiol groups have been used successfully as "alligator clips" in the attachment of molecules of dithiobenzene (a molecule that contains two SH groups) to two gold electrodes simultaneously, with the molecule being used to bridge a gap between the two gold electrodes (6). The same technique can be used for attaching larger molecules, provided that there is a precise match between the length of the molecule and the size of the intermetallic gap.

Sensor Electron Donor (ED) Molecules

In one embodiment of the invention, the electron donor molecule comprises a conjugated pi-orbital system and pendant functional groups that serve as "alligator clips" to attach to electrodes. Examples of sensor molecules suitable for use in a disclosed sensor include a group of ED compounds that can form EDA complexes with nitro-containing compounds, and that are electrically insulating in their normal state, but are electrically conductive when they are bound in an EDA complex. One such molecule is tetrathiafulvalene (TTF) and derivatives thereof. TTF is known to forms conductive (EDA) with tetracyanoquinodimethane, and derivatives of TTF form superconductors (7). TTF also forms EDA compounds with picric acid and with TNT. Tetrathiafulvalene has a formula chosen from at least one of:

wherein R and R' are the same or different and are chosen from a thiol, a phosphate, a carboxylic acid and derivatives thereof, and a siloxane.

Another example of an electron donor molecule suitable for use in the disclosed sensor tetraselenafulvalene (TSeF) or a derivative thereof, the tetraselenafulvalene having a formula chosen from at least one of:

wherein R and R' are the same or different and are chosen from a thiol, a phosphate, a carboxylic acid and derivatives thereof, and a siloxane.

Yet other examples of electron donor molecules suitable for use in constructing a disclosed sensor is at least one member chosen from: dithiophene-tetrathiafulvalene (DT-TTF) or a derivative thereof, the dithiophene-tetrathiaful-valene having a formula chosen from at least one of:

tetrathiatetracene (TTT) or a derivative thereof, the tetrathi-atetracene having a formula chosen from at least one of:

N,N,N',N'-tetramethyl-phenylenediamine (PD), or a derivative thereof, the N,N,N',N'-tetramethyl-phenylenediamine having a formula chosen from at least one of:

trimethoxybenzene (TMB), or a derivative thereof, the trimethoxybenzene having a formula chosen from at least one of:

wherein R and R' are the same or different and are chosen from a thiol, a phosphate, a carboxylic acid, and a siloxane.

The present invention is intended to include sensors comprising all geometric isomers and all positional isomers of the ED molecules described herein.

The invention is not limited to the ED molecules described herein. Other bifunctional, ED molecules can be connected by pendant functional groups to two electrodes. Also suitable for use in an embodiment of the invention is any ED molecule comprising a first moiety capable of bonding to an electrode and a second moiety capable of bonding to a target analyte comprising an electron acceptor molecule to form an EDA complex.

"Alligator Clips", the R and R' Pendant Groups of Sensor ED Molecules

The above-mentioned ED compounds contain pendant groups that enable attachment of the donor molecules to pairs of electrodes. These pendant groups are termed "alligator clips". Such pendant groups include thiols which permit attachment to gold or platinum electrodes. In a sensor disclosed above, R and R' can be thiols chosen from SH and $CH_2(CH_2)_nSH$, wherein n is zero or 1 to 4; and wherein at least one of the first electrode and the second electrode is chosen from gold and platinum.

Another example of a suitable alligator clip for attaching an ED molecule to aluminum electrodes are pendant phosphate groups. In a sensor disclosed above, R and R' can be phosphates chosen from $PO_3H$, $(CH_2)_nPO_3H$, wherein n is 1 to 4; and wherein at least one of the first electrode and the second electrode comprises aluminum.

Pendant carboxylic acids are also alligator clips that permit attachment to aluminum electrodes. In a disclosed sensor wherein at least one of the first electrode and the second electrode comprises aluminum, R and R' can comprise carboxylic acids chosen from $CO_2H$, $(CH_2)_nCO_2H$, wherein n is 1 to 4.

Pendant siloxanes permit attachment of an ED molecule to an electrode coated with a silicon dioxide monolayer. In a sensor according to an embodiment of the invention, R and R' are siloxanes chosen from $Si(OCH_3)_3$, $(CH_2)_nSi(OCH_3)_3$, wherein n is 1 to 4; and wherein at least one of the first electrode and the second electrode comprises a conductive electrode coated with a monolayer of $SiO_2$.

Examples of Sensor Construction and Operation

A disclosed sensor can comprise a plurality of nanojunctions wherein the nanojunctions are in series or in parallel.

Figure 1:
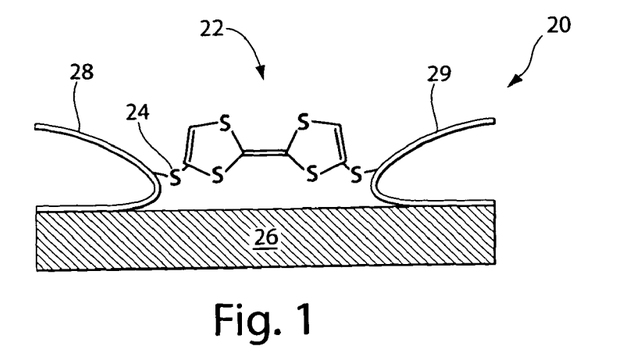
FIG. 1 is a schematic representation of a molecular sensor 20, wherein both electrodes are in contact with the substrate 26, and wherein an electron donor molecule 22 bridges a gap between the electrodes 28, 29, thereby forming a nanojunction.

Turning now to the drawings, a schematic representation of a disclosed molecular sensor 20 is shown in FIG. 1. The sensor 20 comprises a two-terminal molecular device constructed from two metallic electrodes 28, 29 connected to a sensor ED molecule 22 through alligator clips 24. In the illustrated device a TTF molecule is attached to the metallic electrodes via a pair of alligator clips comprising thiols. This device is a poor conductor of electricity with an electrical resistance of 1.25 giga ohms. However, in the presence of one TNT molecule, an EDA complex is formed, with the "sandwiched" structure: metal-(TTF-TNT)-metal. The resulting structure (electrode-EDA complex-electrode) is by far more conductive than the uncomplexed sensor. Also, the capacitance of the sensor changes when an EDA is formed between the sensor electron donor molecule and an explosives-molecule such as TNT.

In the sensor 20 of FIG. 1, the first electrode 28 and the second electrode 29 are each in contact with the non-conductive substrate support 26, and a TTF molecule 22 bridges a gap between the electrodes 28, 29, thereby forming a nanojunction.

Figure 2:
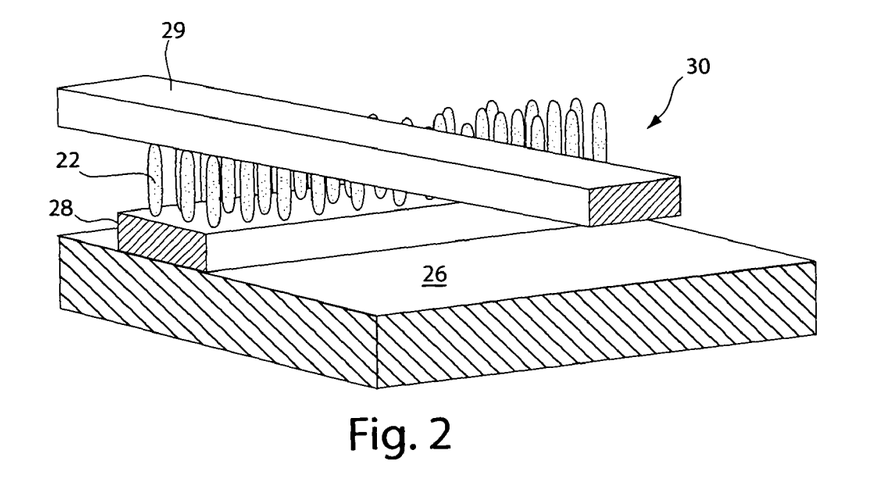
FIG. 2 is a perspective view of a molecular sensor 30, wherein only one electrode 28 is in contact with the substrate 26; the electron donor molecule 22 is oriented such that the length of the molecule is approximately perpendicular to both electrodes.

FIG. 2 is a perspective view representing a molecular sensor 30, wherein the first electrode 28 is in contact with the substrate 26; the ED molecules 22 are oriented such that the length of the molecules 22 is approximately perpendicular to the substrate surface 26 and to both the first electrode 28 and the second electrode 29; and wherein the second electrode 29 is positioned such that the second electrode 29 is not in contact with the substrate 26 and is not parallel to the first electrode 28. In one embodiment of the invention, the second electrode 29 is oriented approximately 90 degrees to the first electrode 28.

To fabricate a sensor as shown in FIG. 2, a first electrode 28 such as, for example, a metal in the form of a wire is first deposited on the surface of a non-conducting support substrate 26 by any one of a number of methods known in the related art. ED molecules 22 are then deposited on top of first electrode 28, such that the ED molecules 22 are standing up, approximately perpendicular to first electrode 28 surface. A second electrode 29, placed at an angle of from about 30 degrees to about 90 degrees is then deposited on top of the ED molecules 22. In a preferred embodiment of a sensor, the second electrode 29 is placed at an angle of about 90 degrees to the first electrode 28. The resulting structure comprises two electrodes with molecules in between the electrodes, and wherein the second electrode 29 does not contact the substrate 26.

Figure 3:
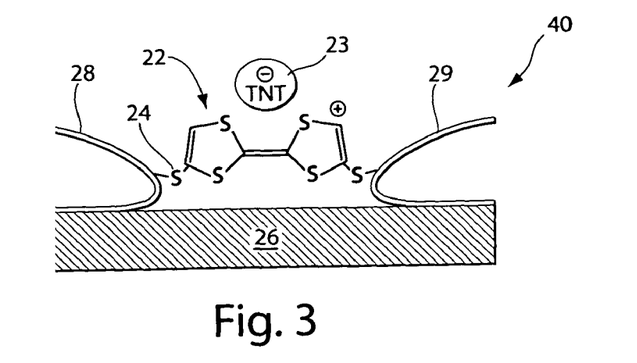
FIG. 3 is a schematic representation of a molecular sensor 40, wherein an electron donor molecule 22 and a TNT analyte 23 have formed an electron donor-acceptor complex.

FIG. 3 shows the molecular sensor 40 with a conductive EDA complex, that forms when the sensor device 20 shown in FIG. 1 comes in contact with a molecule of TNT 23 or other strongly electron-withdrawing molecule. Only one TNT molecule 23, or other nitro-containing molecule is needed to activate the sensor. Thus, the device is very sensitive in detecting a nitro-containing molecule and is able to detect miniscule amounts of explosives.

As stated in the Summary above, a disclosed sensor comprises a detection means operably connected to the pair of electrodes, the detection means capable of detecting a change in the electrical resistance or in the capacitance of the sensor when the ED molecule forms an EDA complex with the nitro-containing explosive molecule, the sensor thereby detecting the presence of the nitro-containing explosive molecule.

The detection means in a disclosed sensor may comprise a chemically sensitive resistor having a resistance that varies in accordance with the resistance of the sensor.

A disclosed sensor may further comprise a conditioning circuitry coupled to the chemically sensitive resistor, the conditioning circuitry capable of generating an analog signal indicative of a change in the resistance of the resistors; an analog-to-digital converter coupled to the conditioning circuitry and capable of providing a digital signal in response to the analog signal; and a control module or data processing unit operably connected to the analog-to-digital converter, the module or unit capable of receiving and processing the digital signal. A disclosed sensor may further comprise a means of attachment to a human or other animal.

EXAMPLE

TTF derivatives containing thiol (SH) pendant groups are prepared from thiolates by deprotection, following the methods described by Becher and co-workers (8). The thiol-protecting groups are 2-cyanoethane. The deprotection is done in situ, namely in place, by the addition of cesium hydroxide monohydrate, dissolved in degassed absolute ethanol. The TTF derivatives are employed as molecular wires and thus contain thiol groups on both rings, to permit bridging between two gold wires that form a gap of from about 1 nanometer (nm) to about 2 nm.

Formation of gold leads is accomplished by e-beam lithography, according to the method described by Guillorn and co-workers (2), or by break-junction techniques as described by Park and co-workers (4).

The rest of the operations are best performed in an environmental chamber in the absence of oxygen.

The substrate, which includes a surface covered with gold electrodes with the proper gaps, is inserted into a solution containing the TTF molecules and the cesium hydroxide. The substrate is left in the solution for 15 minutes and rinsed with degassed ethanol.

Methods of Detection of Analyte

As described above, another aspect of the invention is a method for detecting the presence of a target analyte comprising a nitro-containing explosive molecule. The method comprises:

a) providing a sensor comprising: electrodes made of the same or different materials, and wherein at least one of the electrodes is at the substrate; an ED molecule capable of forming an EDA complex with the nitro-containing explosive molecule; and wherein the ED molecule is disposed between the first electrode and the second electrode and is bonded to the first electrode and to the second electrode, thereby forming a nanojunction between the first and second electrodes; a detection means operably connected to the pair of electrodes, the detection means capable of detecting a change in the electrical resistance or in the capacitance of the sensor when the ED molecule forms an EDA complex with the nitro-containing explosive molecule;

b) exposing the ED molecule of the sensor to an environment containing the nitro-containing explosive molecule such that the nitro-containing explosive molecule contacts the ED molecule;

c) allowing the ED molecule to form an EDA complex with the nitro-containing explosive molecule, the formation of the EDA complex resulting in the sensor undergoing a detectable change in electrical resistance or in capacitance; and d) detecting any change in the electrical resistance or in the capacitance of the sensor, the detected change being indicative of the presence of the nitro-containing explosive molecule in the environment.

According to a disclosed method of detecting the presence of a target analyte, the sensor can comprise any electrode material, including, but not limited to examples of electrode materials described herein. The sensor used in the disclosed method can also comprise any ED molecule capable of forming an EDA complex with a target analyte, including, but not limited to, the ED molecules described herein.

A disclosed method of detecting a target analyte may further comprise: generating an analog signal indicative of the change in the resistance of the resistors; converting the analog signal to a digital signal; transmitting the digital signal to a control module or data processing unit; analyzing the digital signal; and determining whether or not the digital signal exceeds a predetermined threshold value indicative of the presence of the nitro-containing explosive molecule in the environment.

Method of Making a Molecular Sensor

Similarly, according to a disclosed method of making a sensor for detecting the presence of a target analyte comprising a nitro-containing explosive molecule, the sensor can comprise any electrode material, including, but not limited to examples of electrode materials described herein. The sensor used in the disclosed method can also comprise any ED molecule capable of forming an EDA complex with a target analyte, including, but not limited to, the ED molecules described herein.

A disclosed method of making a sensor for detecting explosives molecules can comprise forming the pair of electrodes on the surface of the substrate by E-beam lithography. In another embodiment of a method for making a sensor according to the invention, a pair of electrodesis formed on the surface of the substrate by a break-junction technique comprising: depositing an electrode material as a wire on the surface of the substrate; and bending the substrate, thereby breaking the wire and forming a first and second electrode and an inter-electrode gap.

Yet another embodiment of the disclosed method for making a molecular sensor for explosives comprises forming the pair of electrodes on the surface of the substrate by depositing a gold wire on the surface of the substrate; and applying an electrical current to the gold wire, thereby causing the gold to migrate and break, forming an inter-electrode gap.

The following literature may be useful to investigators in the field of nanometer-sized devices for detecting molecules of explosive compounds:

LITERATURE CITED

1. Foster, *Organic Charge-Transfer Complexes*, Academic Press, Inc., New York, (1969).
2. W. M. Moreau, *Semiconductor Lithography—Principles, Practices, and Materials*, Plenum Press, New York, (1988). Guillorn et al., *J. Vac. Sci. Technol. B*, (2000), 18, 1177.
3. C. Kergueris et al., *Phys. Rev. B*, (2000), 59, 12,505.
4. W. Llang, *Nature*, (2002), 417, 725. Park et al., *Appl. Phys. Lett.* 75, 301 (1999).
5. R. G. Nuzzo and D. L. Allara, *Journal of the American Chemical Society*, (1983), 105,4481; D. L. Allara, et. al., Molecular Electronics, Science and Technology, *Annals of the New York Academy of Sciences*, A. Aviram and M. A. Ratner, Editors, (1998), 852, 349.
6. M. A. Reed, et. al., *Science*, (1997), 278, 252.
7. Hiroo Inokuchi, *Angew. Chem.*, (1988), 100, 1817.
8. N. Sventrup, et. al., *Synthesis*, (1994), 809; E. Gomar-Nadal, et al., *J. Phys. Chem.*, 2004, 108, 7213.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A sensor for detecting the presence of a target analyte comprising a nitro-containing explosive molecule, the sensor comprising:

a support substrate;

a pair of electrodes comprising a first electrode and a second electrode, wherein said first and second electrodes comprise the same or different materials, and wherein at least one of said first and second electrodes is at the substrate;

an electron donor molecule capable of forming an electron donor-acceptor complex with the nitro-containing explosive molecule, wherein the electron donor molecule is chemically bonded to said first electrode and to said second electrode, thereby forming a nanojunction between said first and second electrodes;

a means for detecting a change in the electrical resistance or in the capacitance of the sensor when the electron donor molecule forms an electron donor-acceptor complex with the nitro-containing explosive molecule, wherein said means for detecting a change in the electrical resistance or in the capacitance of the sensor is electrically connected to said pair of electrodes, the sensor thereby detecting the presence of the nitro-containing explosive molecule.

2. The sensor of claim 1, wherein the electron donor molecule comprises a first pendant functional group that is chemically bonded to said first electrode and a second pendant functional group that is chemically bonded to said second electrode, and wherein the first and second pendant functional groups are the same or different.

3. The sensor of claim 2, wherein said first electrode is in contact with the substrate; the electron donor molecule is oriented such that the length of the molecule is approximately perpendicular to the substrate surface and to both said first electrode and said second electrode; and wherein said second electrode is positioned such that said second electrode is not in contact with the substrate and is not parallel to said first electrode.

4. The sensor of claim 3, wherein said second electrode is oriented approximately 90 degrees to said first electrode.

5. The sensor of claim 1, wherein at least one of said first electrode and said second electrode is in the form of a wire.

6. The sensor of claim 1, wherein the nanojunction bridges an inter-electrode distance of from about 0.5 nanometer to about 5 nanometer.

7. The sensor of claim 1, wherein at least one of said first electrode and said second electrode comprises a substance chosen from at least one of gold, platinum, palladium, aluminum, silicon, carbon, Se—Au, and Te—Au.

8. The sensor of claim 7, wherein at least one of said first electrode and said second electrode comprises carbon chosen from at least one of glassy carbon, graphite, carbon paste, and carbon nanotube.

9. The sensor of claim 7, wherein at least one of said first electrode and said second electrode comprises gold in the form of gold nanoparticles.

10. The sensor of claim 1, wherein at least one of said first electrode and said second electrode comprises a conducting oxide.

11. The sensor of claim 10, wherein the conducting oxide is chosen from at least one of platinum oxide, titanium oxide, tin oxide, indium tin oxide, and palladium oxide.

12. The sensor of claim 1, wherein at least one of said first electrode and said second electrode comprises a semiconductor chosen from at least one of silicon doped with at least one element from Group II, Group III, and Group V; and a heterocompound chosen from at least one of a heterocompound comprising elements from Group II, Group III, Group IV, and Group V.

13. The sensor of claim 12, wherein said at least one of said first electrode and said second electrode comprises gallium arsenide.

14. The sensor of claim 1, wherein said at least one of said first electrode and said second electrode comprises a conducting polymer filament.

15. The sensor of claim 1, wherein at least two electron donor molecules are disposed between the first electrode and the second electrode and the molecules are in parallel.

16. The sensor of claim 1, wherein said first electrode and said second electrode are each in contact with the substrate.

17. The sensor of claim 1, comprising a plurality of nanojunctions wherein the nanojunctions are in series or in parallel.

18. The sensor of claim 1, wherein the electron donor molecule comprises a conjugated pi-orbital system and pendant functional groups.

19. The sensor of claim 1, wherein the electron donor molecule comprises tetrathiafulvalene or a derivative thereof, the tetrathiafulvalene having a formula chosen from at least one of:

wherein R and R' are the same or different and are chosen from a thiol, a phosphate, a carboxylic acid and derivatives thereof, and a siloxane.

20. The sensor of claim 19, wherein R and R' are thiols chosen from SH and $CH_2(CH_2)_n SH$, wherein n is zero or 1 to 4; and wherein at least one of said first electrode and said second electrode is chosen from gold and platinum.

21. The sensor of claim 19, wherein R and R' are phosphates chosen from $PO_3H$, and $(CH_2)_n PO_3H$, wherein n is 1 to 4; and wherein at least one of said first electrode and said second electrode comprises aluminum.

22. The sensor of claim 19, wherein R and R' are carboxylic acids chosen from $CO_2H$, and $(CH_2)_n CO_2H$, wherein n is 1 to 4; and wherein at least one of said first electrode and said second electrode comprises aluminum.

23. The sensor of claim 19, wherein R and R' are siloxanes chosen from $Si(OCH_3)_3$, and $(CH_2)_n Si(OCH_3)_3$, wherein n is 1 to 4; and wherein at least one of said first electrode and said second electrode comprises a conductive electrode coated with a monolayer of $SiO_2$.

24. The sensor of claim 1, wherein the electron donor molecule comprises tetraselenafulvalene or a derivative thereof, the tetraselenafulvalene having a formula chosen from at least one of:

wherein R and R' are the same or different and are chosen from a thiol, a phosphate, a carboxylic acid and derivatives thereof, and a siloxane.

25. The sensor of claim 1, wherein the electron donor molecule is at least one member chosen from: dithiophene-tetrathiafulvalene or a derivative thereof, the dithiophene-tetrathiafulvalene having a formula chosen from at least one of:

tetrathiatetracene or a derivative thereof, the tetrathiatetracene having a formula chosen from at least one of:

-continued

N,N,N',N'-tetramethyl-phenylenediamine, or a derivative thereof, the N,N,N',N'-tetramethyl-phenylenediamine having a formula chosen from at least one of:

-continued trimethoxybenzene, or a derivative thereof, the trimethoxybenzene having a formula chosen from at least one of:

wherein R and R' are the same or different and are chosen from a thiol, a phosphate, a carboxylic acid, and a siloxane.

26. The sensor of claim 25, wherein R and R' are thiols chosen from SH and $CH_2(CH_2)_nSH$, wherein n is zero or 1 to 4; and wherein at least one of said first electrode and said second electrode is chosen from gold and platinum.

27. The sensor of claim 25, wherein R and R' are phosphates chosen from $PO_3H$, $(CH_2)_nPO_3H$, wherein n is 1 to 4; and wherein at least one of said first electrode and said second electrode comprises aluminum.

28. The sensor of claim 25, wherein R and R' are carboxylic acids chosen from $CO_2H$, $(CH_2)_nCO_2H$, wherein n is 1 to 4; and wherein at least one of said first electrode and said second electrode comprises aluminum.

29. The sensor of claim 25, wherein R and R' are siloxanes chosen from $Si(OCH_3)_3$, $(CH_2)_nSi(OCH_3)_3$, wherein n is 1 to 4; and wherein at least one of said first electrode and said second electrode comprises a conductive electrode coated with a monolayer of $SiO_2$.

30. The sensor of claim 1, wherein the detection means comprises a chemically sensitive resistor having a resistance that varies in accordance with the resistance of the sensor.

31. The sensor of claim 30, further comprising:
a conditioning circuitry coupled to the chemically sensitive resistor, the conditioning circuitry capable of generating an analog signal indicative of a change in the resistance of the resistors;
an analog-to-digital converter coupled to the conditioning circuitry and capable of providing a digital signal in response to the analog signal;
a control module or data processing unit operably connected to the analog-to-digital converter, the module or unit capable of receiving and processing the digital signal.

32. The sensor of claim 1, further comprising a means for attaching the sensor to a human or an animal.

33. The sensor of claim 1, wherein the electron donor molecule is electrically insulating in its normal state.

* * * * *